United States Patent [19]
Kamentsky et al.

[11] Patent Number: 5,427,910
[45] Date of Patent: Jun. 27, 1995

[54] METHOD OF CYTOGENETIC ANALYSIS

[75] Inventors: Louis A. Kamentsky, Boston; Lee D. Kamentsky, Arlington, both of Mass.

[73] Assignee: CompuCyte Corporation, Cambridge, Mass.

[21] Appl. No.: 987,679

[22] Filed: Dec. 9, 1992

[51] Int. Cl.$^6$ .............................................. C12Q 1/68
[52] U.S. Cl. .................................... 435/6; 435/810; 436/501; 436/63; 935/77; 935/78
[58] Field of Search ................ 435/6, 91, 810, 91.1, 435/912; 436/501, 63; 536/22.1, 23.1, 24.1, 24.2, 24.31–24.33; 935/78, 77

[56] References Cited

U.S. PATENT DOCUMENTS 4,710,465  12/1987  Weissman et al. ............... 435/91
5,072,382  12/1991  Kamentsky ................. 364/413.08

OTHER PUBLICATIONS

Lichter et al. (1988) Proc. Nat'l Acad. Sci (USA), vol. 85, pp. 9664–9668.
Cell Biology (1974) (Published by Alhyn and Bacon, Inc., Boston) ed. by Robert Dyson, pp. 418 and 419.
Emmerich et al., Exp. Cell Res., 181:126–140 (1989).
Devilee et al., Cytogenet. Cell Genet., 41:193–201 (1986).
Donis-Keller, et al., Cell, 51:319–337 (1987).
Gerhard, et al., P.N.A.S., USA, 78:3755–3760 (1981).
Harper et al., Chromosoma, 83:431–491 (1981).
Higgins et al., Chromosoma, 93:77–86 (1985).
Kallioniemi et al., P.N.A.S., USA, 89:5321–5325 (Jun. 1992).
Nederlof, et al., Cytometry, 11:126–131 (1990).
Pinkel et al., P.N.A.S., USA, 85:9138–9142 (1988).
Popp et al., Exp. Cell Res., 189:1–12 (1990).
Roberts, Science, 254:378–379 (1991).
Singer et al., P.N.A.S., USA, 79:7331–7335 (1982).
Waye et al., Mol. Cell Bio., 7:349–356 (1987).
Waye et al., Nucleic Acids Res., 14:6915–6927 (1986).
Yang et al., P.N.A.S., USA, 79:6593–6597 (1982).

*Primary Examiner*—Margaret Parr
*Assistant Examiner*—Ardin H. Marschel
*Attorney, Agent, or Firm*—Fish & Richardson

[57] ABSTRACT

A method of characterizing the chromosomes in a sample of cells by fixing the cell sample on a substrate, contacting the cell sample with a nucleic acid probe having a detectable label under conditions that allow the probe to hybridize preferentially to a chromosome in the cells to form a hybridized complex, optically detecting each labeled complex in the sample, defining a predetermined number of neighboring labeled complexes as a group, generating a distance parameter based on the distance between the position of a group and the position of the next neighboring labeled complex, and comparing the distance parameter for each group to a standard distance value to characterize the chromosomes in the cells of the sample.

22 Claims, 8 Drawing Sheets

Peak Fluorescence versus Spot Distance

Spot Count per Spot Distance Value

Region Spot Count / Total Count = 1120/3983 = 28.1%

FIG. 7A X Male

Region Spot Count / Total Count = 2935/3942 = 74.4%

FIG. 7C X Female

Peak Fluorescence versus Spot Distance    Spot Count per Spot Distance Value
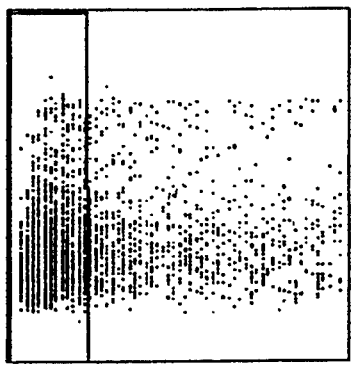 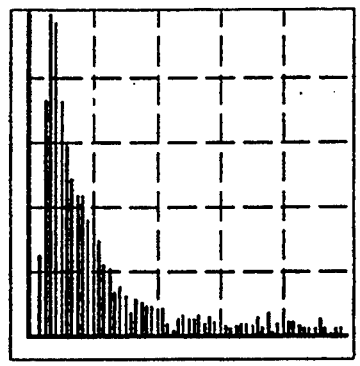
Region Spot Count / Total Count = 1994/3816 = 52.3%
FIG. 8A   X Female                FIG. 8B
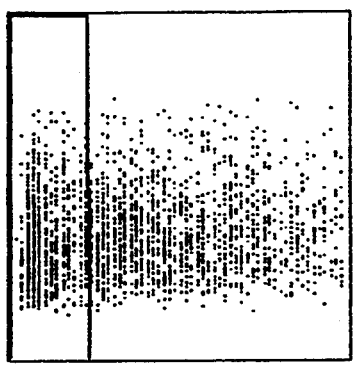 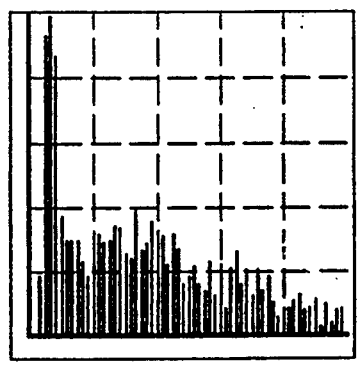
Region Spot Count / Total Count = 854/3932 = 21.7%
FIG. 8C   X Male                  FIG. 8D
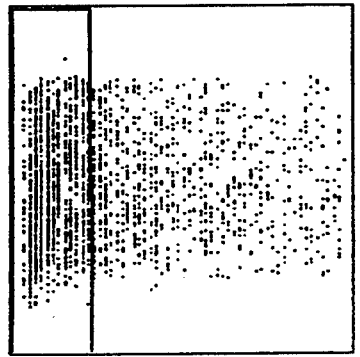 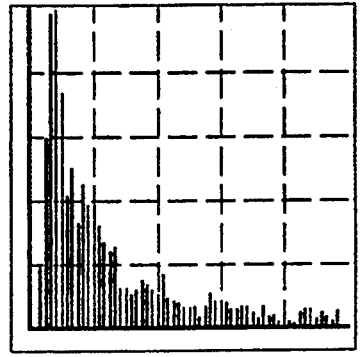
Region Spot Count / Total Count = 1380 / 3970 = 34.8%
FIG. 8E   50% Female - 50% Male X   FIG. 8F

METHOD OF CYTOGENETIC ANALYSIS

BACKGROUND OF THE INVENTION

The invention relates to determining the presence of chromosomal abnormalities, such as abnormal numbers of specific chromosomes, in cells.

All cells contain DNA comprising the genetic information necessary to control a cell's biologic function. DNA is made up of two linear strands of four different chemical building blocks or nucleotides arranged in specific sequences which are translated by mechanisms in cells to control the manufacture of specific proteins such as enzymes. The total of the some 100,000 genes in humans, each of which codes for one specific protein, constitute the genome of an individual. These genes are organized into rod-like chromosomes which can be visualized microscopically for only a brief time in a cell's life cycle, during the so-called metaphase, which is just prior to cell division. In humans, each cell contains 46 chromosomes, 23 of which are contributed by each parent. As a result, many genes occur on two different chromosomes and are located at two separated positions in the interphase cell nucleus.

Medical research has shown links between flaws in specific genes or chromosomes and certain diseases. Of major importance are gene modifications causing cancer or birth defects such as Down's syndrome, or a predisposition to certain cancers. Such genetic modification may take any of the following forms: 1) aneuploidy, an abnormal number of one of the 23 chromosomes; 2) translocations, genetic material moved to a wrong chromosome; 3) rearrangement mutations, genetic material moved to the wrong place on a chromosome; 4) amplifications, an abnormal number of copies of a specific gene; 5) deletion mutations, a specific gene segment is missing; and 6) point mutations, altered nucleotides in a gene sequence. Of particular interest are mutations of genes which may enhance or suppress tumor growth, the so-called oncogenes and tumor suppressor genes.

It is important to identify such genetic modifications to diagnose or predict certain diseases. For example, chromosome banding techniques are widely used to identify numerical and/or structural chromosome aberrations in tumor and prenatal diagnosis. However, the interpretation of the banding patterns requires skilled technicians, is often complicated by imperfect banding, chromosome condensation, and limited numbers of metaphases, and is difficult, e.g., in cases of highly aneuploid tumors with extensive structural changes.

An alternative method to detect chromosomal aberrations is an in situ hybridization technique, which uses chromosome-specific probes to analyze nuclear DNA directly when the cells are in interphase. A variation of this method, called fluorescent in situ hybridization (FISH), also involves a nucleic acid probe with a defined nucleotide sequence that preferentially hybridizes with a specific complementary nucleotide sequence of DNA, or target DNA, on one or more chromosomes in a cell. The target nucleotide sequence may be unique or repetitive, as long as it can be used to distinguish one or more specific chromosomes. In the FISH technique, the probe is marked with a fluorescent label so that cells with the target DNA sequence(s), to which the marked probes hybridize, can be detected microscopically. Each chromosome containing the target DNA sequence(s), and hence the marked probe, will emit a fluorescent signal or spot in every cell.

For example, a cell sample allowed to hybridize with a fluorescently labeled DNA probe that hybridizes to a specific target nucleotide sequence on chromosome number 21 will show two fluorescent spots in each cell from a normal person, and three spots in each cell from a Down's syndrome patient, because these patients have an extra chromosome number 21. Probes specific for chromosome 21 are well known. See, e.g., Pinkel et al., P.N.A.S., USA, 85:9138-9142 (1988), which is incorporated herein by reference.

The six different genetic abnormalities described above are detected by the FISH technique as follows. Aneuploidy is determined by counting spots per cell using a DNA probe specific to one chromosome. Translocations and rearrangements are determined by using DNA probes covering the translocation or rearrangement and a neighboring sequence and determining whether the spots from each sequence are separated or concentric. Amplification, deletion, and point mutations are determined by quantifying the fluorescence from spots using FISH for a specific target nucleotide sequence.

The FISH technique can be used for a variety of diagnostic and screening tests. For example, it can be used in conjunction with techniques such as amniocentesis and chorionic villus sampling (CVS) to screen fetuses to determine whether the baby will have a serious birth defect such as Down's syndrome. Both amniocentesis and CVS are associated with the risk of miscarriage, which may be minimized by the FISH technique. This risk is estimated at 1.0% to 2.0% for CVS and at 0.5% for amniocentesis. It may soon be possible to sidestep that risk entirely by obtaining fetal cells from the mother's blood, so that only a blood sample rather than an umbilical cord sample is required.

To apply the FISH technique as a prenatal screening tool, sets of DNA probes may be used that hybridize to regions of five different chromosomes, e.g., 21, 18, 13, X, and Y, which together account for 90% to 95% of all birth defects related to chromosomal abnormalities.

There are also FISH tests proposed for cancer screening, diagnosis, prognosis, and treatment monitoring in which the presence or the absence of specific gene sequences must be determined in patient cell samples. Such screening and diagnosis currently requires technicians to visually count fluorescent spots in each cell under a microscope. However, such manual microscopic visualization is quite laborious and is therefore not currently performed on a routine basis.

SUMMARY OF THE INVENTION

The invention features an automated method of generating different properties of a large population of cells in a sample treated using the FISH technique, which can indicate and display for every cell 1) the number of copies of a specific DNA sequence, 2) the number of chromosomes containing this sequence, and 3) whether two different sequences are contiguous. Generation of these properties by applicants' apparatus will allow automation of cytogenetic screening for birth defects and the use of DNA probes for cancer screening, diagnosis, treatment, determination, and monitoring.

Applicants have discovered that the automation of laboratory tests using the FISH technique may be carried out with applicants' apparatus which can quantify two aspects of the fluorescence emanating from cells treated with the FISH procedure. First, it determines the amount of fluorescence resulting from each FISH spot to quantify the number of copies of a target DNA sequence. Second, it determines the number of spots in each cell to determine how many chromosomes contain the specific DNA sequences, or if the spots are concentric.

In general, the invention features a method of characterizing the chromosomes in a sample of cells, e.g., from a mammal or a fetus, by fixing the cell sample on a substrate, contacting the cell sample with a nucleic acid probe having a detectable label, e.g., a fluorescent label such as fluorescein, CY3, rhodamine, or CY5, under conditions that allow the probe to hybridize preferentially to a target nucleotide sequence within one or more chromosomes in the cells to form hybridized complexes, wherein each complex forms a labeled region, detecting each labeled region in the sample, assigning a position on the substrate to each detected labeled region, defining a predetermined number of neighboring, e.g., nearest adjacent, labeled regions as a region group and assigning a position on the substrate to each region group which is related to the positions of each of the regions within the group, generating a distance parameter based on the distance between the position of a region group and the position of the next neighboring labeled region and recording the distance parameter for each region group in the sample, and comparing the distance parameter for each region group to a standard distance value to characterize the chromosomes in the cells of the sample.

An alternative method of calculating and recording a distance parameter is to define a predetermined number N of labeled regions as a region group, generate a distance parameter for a labeled region based on the distance between the position of the labeled region and the position of the Nth closest labeled region, and recording the distance parameter for each labeled region in the sample.

The phrase "hybridize preferentially to a specific nucleotide sequence" means that a given nucleic acid probe will hybridize selectively with the target nucleotide sequence or sequences within a specific chromosome more stably than with other sequences in any other chromosome under the same hybridization conditions. This selectivity is based on the nucleotide sequence of the probe, which is complementary to the target nucleic acid sequence or sequences. Nucleic acid hybridization is based on the ability of two nucleic acid strands to pair at their complementary segments to form hybridization complexes. The formation of these complexes can be made highly specific (preferential) by adjustment of the hybridization conditions (stringency) such that hybridization will not occur unless the probe and the target sequence are precisely complementary.

The term "region" means a specific set of digital data points that statistically encompass the optical signal from the label of one hybridized complex. That is, on average, only one set of digital data points corresponding to one complex will be located within a region. A "region group" is a set of one, two, or more, regions that are combined and processed as one group.

In a preferred embodiment, the target nucleotide sequence is unique to a specific chromosome, the standard distance value is based on the cellular nuclear diameter, the predetermined number of neighboring labeled regions in a region group is two, and the comparison step provides a determination of the number of chromosomes in the cells of the sample. Under these conditions, a distance parameter greater than the standard distance value indicates two chromosomes per cell, and a distance parameter less than the standard distance value indicates more than two chromosomes per cell. For example, when the target sequence is unique to chromosome 21, cells having more than two chromosomes per cell indicate Down's Syndrome.

As used herein, a target nucleotide sequence that is "unique to a specific chromosome" is a single copy or highly repetitive nucleotide sequence that is found only on one specific chromosome, or in such a concentration or copy number on one chromosome that it can be used to distinguish that chromosome from other chromosomes that may have a lower concentration of the same or a similar sequence.

In another embodiment, the target nucleotide sequence is unique to a specific chromosome, the standard distance value is based on the cellular nuclear diameter, the predetermined number of neighboring labeled regions in a region group is one, and the comparison step provides a determination of the number of chromosomes in the cells of the sample. In this case, a distance parameter greater than the standard distance value indicates one chromosome per cell, and a distance parameter less than the standard distance value indicates more than one chromosome per cell. For example, when the target sequence is unique to chromosome X, cells having one chromosome per cell are from a male.

In another embodiment, the standard distance value is based on the cellular nuclear diameter, the predetermined number of neighboring labeled regions in a region group is greater than one, and the comparison step provides a determination of a chromosomal abnormality in the cells of the sample. Under these conditions, a distance parameter greater than the standard distance value indicates the predetermined number of neighboring labeled regions per cell, and a distance parameter less than the standard distance value indicates more than the predetermined number of neighboring labeled regions per cell.

In preferred embodiments, the target nucleotide sequence may be unique to a specific genetic abnormality, and more than one type of probe may be used, each type of probe hybridizing preferentially to a unique target nucleotide sequence of one or more chromosomes in the cells, and each type of probe having a unique detectable label.

In further embodiments, the method may further include the step of defining a threshold level below which no label is detected, and the label detecting step may include measuring a level for each label in the sample, if any, and comparing the label level with the threshold level, a label being detected only when its level is above the threshold level.

The invention also features a method of characterizing the chromosomes in a sample of cells by (a) fixing the cell sample on a substrate, (b) contacting the cell sample with a nucleic acid probe comprising a detectable label under conditions that allow the probe to hybridize preferentially to a target nucleotide sequence within one or more chromosomes in the cells to form labeled hybridized complexes, (c) scanning the cell sample with a laser beam to generate an optical, e.g., fluorescent, signal, (d) detecting the optical signal and digitizing the detected signal to produce a set of digital data points, (e) storing the set of digital data points, (f) locating a region within a stored set of digital data points, this region including contiguous data points with digital values above a predetermined threshold value, this region representing one labeled complex, (g) assigning a position on the substrate to each region, (h) defining a predetermined number of neighboring regions as a region group and assigning a position on the substrate to each region group which is related to the positions of each of the regions within the group, (i) generating a distance parameter based on the distance between the position of a region group and the position of the next neighboring region, (j) recording the distance parameter for each detected region group, and (k) processing the distance parameters to characterize the chromosomes in the cells of the sample.

The processing step of this method may include the steps of (a) summing the digital values in each region for each probe, and (b) recording the summed digital values for each probe, wherein these values are proportional to the DNA copy number. Furthermore, an alternative method of calculating the distance parameter is to define a predetermined number N of regions as a region group, and generate a distance parameter for a region based on the distance between the position of the region and the position of the Nth closest region.

In a further preferred method, the standard distance value is based on an inter-chromosomal distance, the predetermined number of neighboring regions is one, the combining step involves a first probe which hybridizes preferentially to a first target nucleotide sequence normally within a first chromosome, and a second probe which hybridizes preferentially to a second target nucleotide sequence normally within a second chromosome, and the processing step involves a comparison of the distance parameter with the inter-chromosomal distance to determine the presence of translocations of the first and second nucleotide sequences in the cells of the sample. Under these conditions, a distance parameter less than the standard distance value indicates a translocation.

The method also allows the manual or automatic movement of the microscope stage to an assigned position of a region having a specific distance parameter so that the operator may observe cells visually.

In the methods of the invention, the position assigned to a region group may be, for example, proportional to an average of the positions of peak intensity value of each region in the region group.

The invention also features a method in which the contacting step involves a first probe which hybridizes preferentially to a first target nucleotide sequence and comprises a first label, and a second probe which hybridizes preferentially to a second target nucleotide sequence and comprises a second label, and wherein the first probe is scanned in the cell sample with a laser beam having a first wavelength which excites the first label, and the second probe is scanned in the cell sample with a laser beam having a second wavelength which excites the second label. In this method, the first wavelength and second wavelength laser beams may scan the cell sample at different times, e.g., sequentially.

Other features and advantages of the invention will be apparent from the following description of the preferred embodiments, and from the claims.

BRIEF DESCRIPTION OF THE DRAWING

FIGS. 7A–D are a series of monitor displays of fluorescent spot count and distance parameters for X chromosomes in male and female cell samples.

FIGS. 8A–E are is a series of monitor displays similar to FIGS. 7A–D, for male, female, and mixed gender cell samples.

DESCRIPTION OF THE PREFERRED EMBODIMENTS

Mechanical and Optical Systems

The hardware of the laser scanner microscope described in U.S. Pat. Nos. 5,072,382 and 5,107,422 (the "Kamentsky et al. patents"), which are incorporated herein by reference, is the preferred apparatus to carry out the method of this invention.

Figure 1:
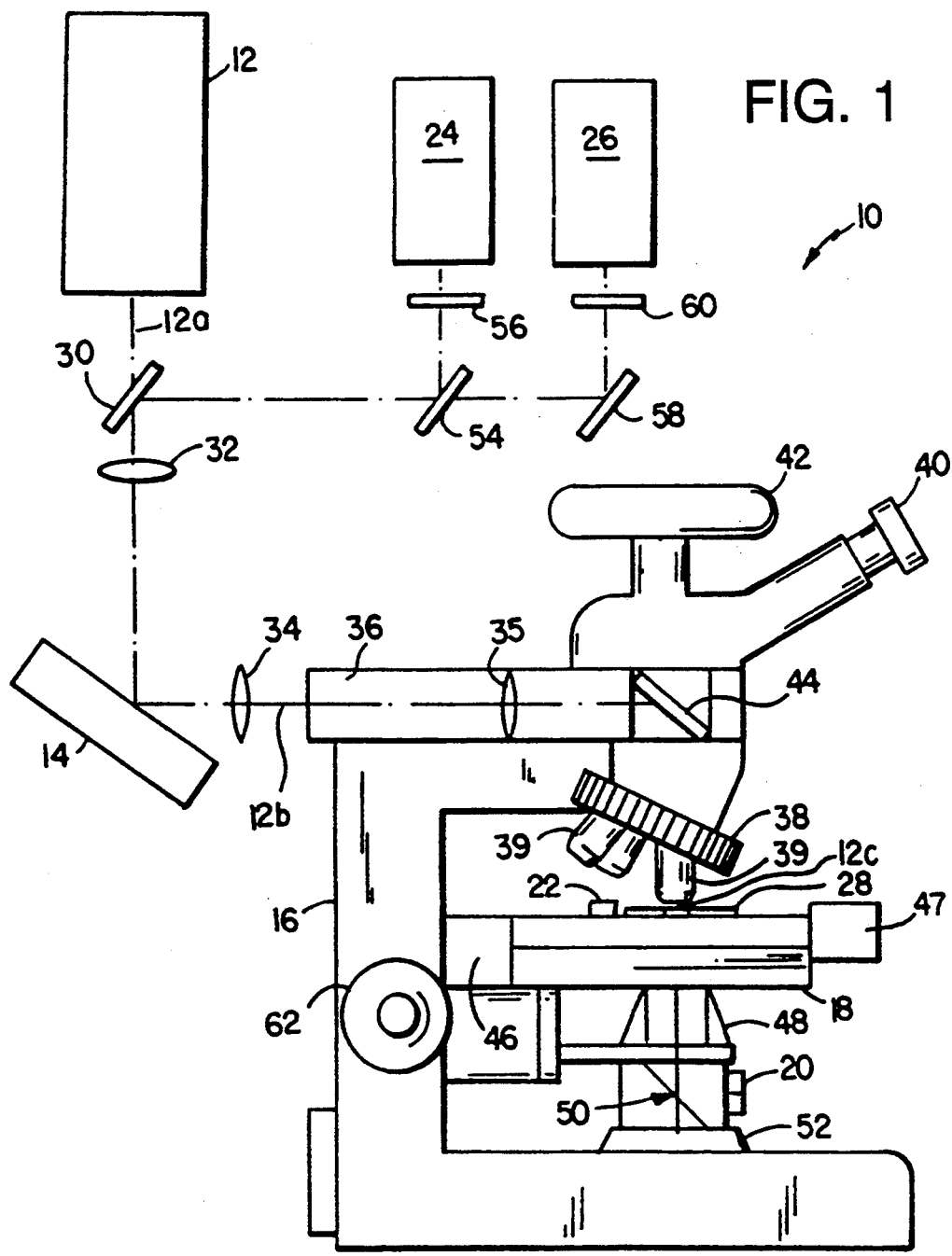
FIG. 1 is a schematic diagram of an instrument for measuring optical signals from cell samples at high rates of speed.

Referring to FIG. 1, the instrument 10 includes a light source 12, a mirror scanner 14, such as a resonant galvanometer scanner, an epi-illumination microscope 16, a stepper motor controlled stage 18, light detectors 20, 22, 24, 26, and various associated optical components which will be described below. Light source 12 produces a light beam 12a that reflects off of scanner 14 to produce a scan beam 12b and finally illuminates a scan spot 12c of a fixed diameter or size on a specimen plane or surface 28. Specimen plane or surface 28 is positioned on stage 18. Light source 12 is a laser such as, for example, a Helium-Neon, Helium-Cadmium, solid state, or Argon ion laser, depending on the application.

More than one laser may be used for a given application, in which case, the beams can be combined using a dichroic mirror so that they are coaxial. For some applications it may be desirable to control the intensity of the laser beams or shutter them under the control of a computer. Lasers with multiple wavelength outputs may also be used, in which case, it may be desirable to use a computer-controlled filter, prism or Bragg cell to select a specific wavelength.

In the preferred embodiment, the laser is preferably a Helium-Neon laser emitting in the green wavelength (542 nm) when used with the fluorescent dye CY3, which fluoresces in the red wavelength (590 nm). An Argon ion laser emitting in the blue wavelength (488 nm) may be used in conjunction with the dye fluorescein, which fluoresces in the green wavelength (530 nm).

After passing through a dichroic mirror 30, the laser beam is imaged by two lenses 32 and 34 onto an epi-illumination field stop 36 of microscope 16. Resonant scanner 14 is located between lenses 32 and 34 and scans the beam across the field stop when electrically driven. The focal lengths of lenses 32 and 34 and the deflection angle of scanner 14, which is proportional to the galvanometer drive voltage, control the size of the spot and the length of the scan at field stop 36 and thus, at surface 28.

Slides containing cells are preferably scanned with a spot size of approximately 2 microns using a 40X objective lens. The scanner is driven at 800 Hz and the scan length at the specimen is 100μ. These are nominal values and can be changed by the user by rotating microscope nosepiece 38 bearing objectives 39 from 40X to other higher magnifications to reduce the spot size and scan length or lower magnifications to increase them.

Epi-illumination is used to illuminate the specimen and to transmit fluorescent light to the viewing eyepiece 40 or to a film or video camera 42. The light transferring assembly 44 may contain a dichroic or partially or fully silvered mirror as well as an optical filter in the viewing path. These assemblies are interchangeable and the microscope used in the described embodiment includes a movable rod to exchange these assemblies.

Specimen surface 28 may be a slide upon which a tissue or cytology specimen is mounted.

The FISH technique results in one or more optical signals, i.e., fluorescent spots, of approximately 2 microns diameter each, that are emitted by the label of the nucleic acid probes hybridized to a specific complementary target DNA sequence on a chromosome in the cell nucleus. Each signal represents one such hybridized complex. One or more fluorescence parameters, e.g., in the wavelength range 460 to 650 nm, are measured by the laser scanner microscope. The sampling rate is selected to be 150 KHz digitizations per second, which results in sampling the fluorescence optical signal at spatial intervals of approximately 1μ that are smaller than the spot size taught in the Kamentsky et al. patents. Although the FISH technique uses fluorescent stains, the present invention may be carried out using other stains that can be optically detected, e.g., horseradish peroxidase.

Optical, e.g., fluorescent, signals from the cell sample are collected by objective lens 38 at high numerical aperture and imaged back through the lenses 35, 34, and 32 to dichroic mirror 54 which is designed to reflect the fluorescent wavelengths. Dichroic mirror 30 transmits almost all of the laser wavelength and reflects the fluorescent wavelengths. Dichroic mirror 54 splits the light into two parts so as to measure two different wavelengths of fluorescence. Mirror 54 reflects part of the incident energy through filter 56 of the appropriate bandpass wavelength onto photomultiplier 24. Similarly, mirror 58 reflects the remaining energy through filter 60 to photomultiplier 26. The signals from the two photomultipliers are amplified and become inputs for the data acquisition circuit.

The position of the cell sample with respect to scanning beam 12b is controlled by X and Y stepping motors 46, 47. The X motor is driven in steps that are of a size ranging from a fraction of the spot size to the spot size. This step size is under the control of a computer program. The stage is also provided with sensors to provide signals to the computer to indicate a "Home" or reference position for the stage and to limit its travel. By always moving the stage to Home at the beginning of each run or periodically during a run (i.e., a group of scan strips), it is possible to obtain the absolute position of given cells on the specimen surface so they can be manually reviewed or remeasured. For normal use, the stage can be moved manually by knobs attached to the motors. The stage may also be manually controlled by buttons, a joystick or a computer mouse with a specifically programmed display. The microscope 16 is focused manually by knob 62.

Electromechanical System

Figure 2:
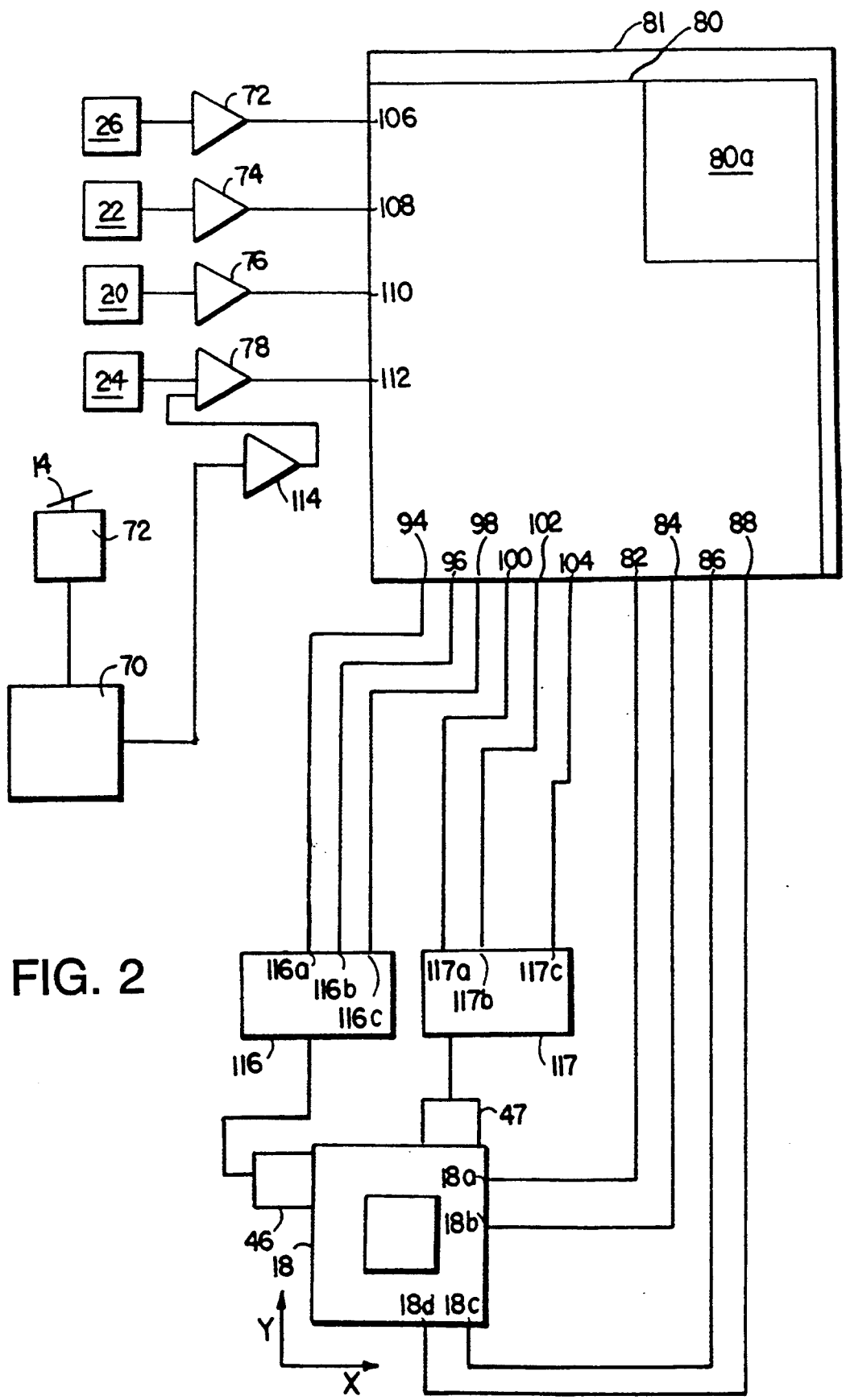
FIG. 2 is a block diagram of the electromechanical circuit used in the instrument shown in FIG. 1.

Referring to FIG. 2, the electromechanical system provides means of inputting signals from the light sensors 20, 22, 24 and 26, the scanner driver 70, and the microscope stage 18, to the computer 81 and outputting signals from the computer to the X stepper motor 46 and Y stepper motor 47 which move the microscope stage 18. As used for the method of this invention, photomultipliers 24 and 26 are used to detect analog optical, e.g., fluorescence, signals. Two commercially available circuit boards 80, which accept four analog voltages, digitize them at rates up to 200,000 Hz with analog-to-digital converter 80a, and cause the resultant digital data to be stored in the computer memory under direct memory access (dma) control are used to control the entire system. Boards 80 also accept digital values from inputs 82–88, which provide limit information from the stage, and provide digital output values on lines 94–104, which control the stage. This also controls the values of two analog voltages used to control the supply voltages to photomultipliers (light detectors) 24 and 26. A detailed description is available in the Kamentsky patents.

The position of the scanning mirror 14 may be synchronized with the data acquired by the sensors and converted to a stream of digital data. The digital data stream for a scan may be stored in contiguous blocks of memory. For synchronization purposes, the D.C. level of circuit 78 is initially set so that a negative synchronization pulse is easily detected. Synchronization is accomplished by using a pulse synchronization signal generated by the scanner mirror driver 70 which controls the motion of scan mirror 14 through scanner 72. The synchronization signal may be added to the sensor signal from sensor 24, or used as a separate input signal. The signal at input 112 is the fluorescence signal of sensor 24 and the pulse signal is negatively added near one scan extreme. This synchronization pulse is detected by the program and used to properly synchronize the digital data stored in the computer memory.

The sampling rate is set by the user through an initialization program which allows the user to define a protocol for each test. The protocol is monitored on a screen that the operator uses to set the sampling rate and the various test parameters, area scanned, threshold settings, etc. The number of parameters digitized is also preset and the amplifier gain settings and input/output relationship, i.e., linear or logarithmic, may be used as additional parameters.

The levels of the digital outputs 94, 96, 98, 100, 102 and 104, of circuit boards 80 are under the control of the computer program. The digital inputs 82, 84, 86, and 88 are read at specific times also determined by the control of the program. These outputs and inputs are used to control the movement of the microscope stage 18 via X stepper motor 46 and Y stepper motor 47, which are each driven by translator circuits 116 and 117, respectively. The microscope stage is provided with limit switches which indicate when the stage has reached its limit of travel in the x and y directions. These switches generate signals on lines 18a–18d which are used as inputs 82 to 88, respectively, of boards 80. Although not shown here, additional digital outputs may be used to control the wavelength of the light source by controlling specific light sources, shutters, or filter positions.

Figure 3:
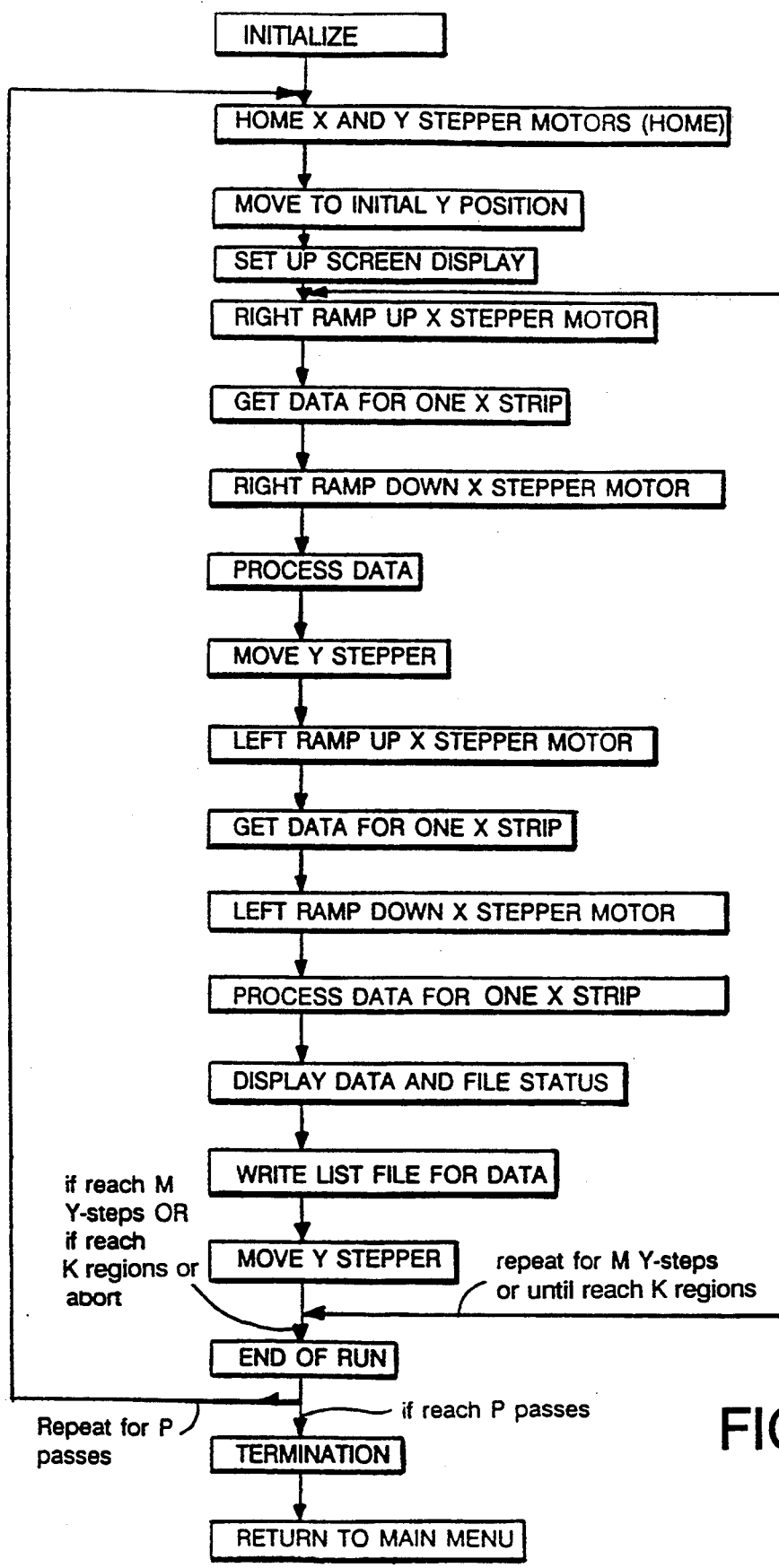
FIG. 3 is a flow chart of the general optical signal data acquisition loop.

The program controlled stage motion is designed to perform the following sequence that is depicted in the flow chart of FIG. 3. First, when the user initiates a test, both stepper motors are moved to a specific "Home" position. This is accomplished by calling a program subroutine to pulse lines 94 and 100 on and off until inputs 82 and 88 indicate that the stage has reached Home. Under program control, outputs 96 and 102 are set to produce the proper stage direction by producing signals received at inputs 116b and 117b. As soon as the stage reaches Home, the Y stepper is pulsed to move the stage 18 to the initial y position, then a subroutine is called to move the stage to the right in the x direction by changing the signal on output 96. In one embodiment, the pulse rate on output 94 is ramped-up in rate from about 100 up to 1600 pulses per second (pps) for a fixed total number of pulses or distance, typically 100 pulses or steps. This is the ramp-up number. This fixed ramp-up and the final step rate may also be adjusted by the program or by a commercially available ramp-up controller circuit (Metrobyte, Taunton, Mass.).

The program typically produces a rate of 1600 pps, at the end of the ramp-up, so the stepper is moving at full stepping speed at this time. The X step size is 1 micron so that the stage is preferably moving at the rate of one step per scan. The stepping motion in conjunction with the scanning motion generated by scanner driver 70 which is perpendicular to the stepping motion creates the scan pattern shown in FIG. 4.

Figure 4:
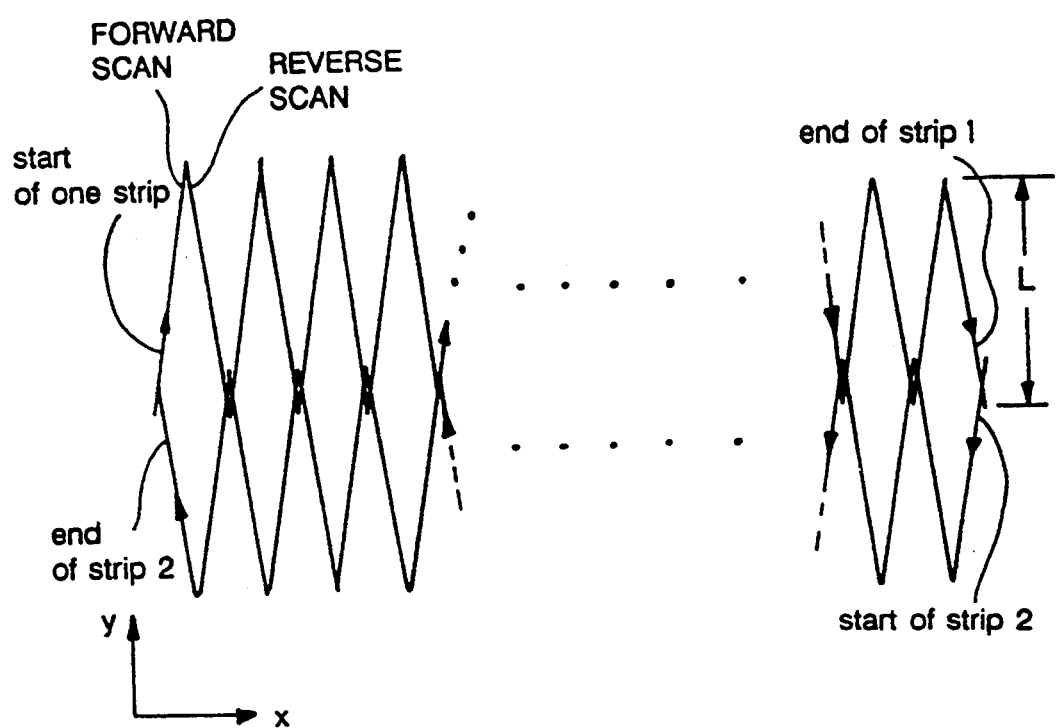
FIG. 4 is a schematic drawing of the scan pattern of the laser beam.

In FIG. 4, the scan starts at the left, at the Home position, and forward and reverse scans of length "L" are produced until the end of one scan strip is reached. Such a strip typically encompasses 5000 forward and 5000 reverse scans.

An additional parameter of the protocol is the X scan distance. This distance determines the length of one scan strip. This length can be used to calculate the size required for the data buffers by multiplying the number of parameters measured by the total number of data values digitized per scan strip. The boards 80 digitize inputs and store them in a buffer. At this time the boards 80 send 100 pulses to the X stepper to ramp it down in velocity to a stop. The digital data in the buffers may be processed at the end of a complete scan strip, as will be described below, or it may be processed as the next strip is being digitized. At the conclusion of this scan strip, stepper motor 47 moves the stage in the y direction so that a new scan strip can be run. Output 100 is used to send pulses to input 117a to step the motor; output 102 determines whether movement is in the positive or negative y direction and output 104 determines the size of the steps (5 or 10μ) and passes a signal to input 117c. Again, smaller or larger movements may be used under protocol control.

After stepping the Y motor 47 to move the specimen "up" or "down" in the y direction a distance equal to 60% of the scan length L, as shown in FIG. 4, the procedure described above, in which the X stepper motor 46 is ramped up in rate and moved the X distance, and ramped back down to a stop is repeated but the stage is moved back to the left in the x direction. The Y stepper then moves the stage in the y direction a number of steps and the complete cycle is repeated. The number M of Y steps are counted by the program and the test is terminated when the Y distance is reached as determined by the user through the appropriate protocol parameter.

Preparation of the Probes

Probes typically used in FISH assays are suitable for use in the methods of the invention. For example, probes specific for different human chromosomes, under the proper stringency conditions, are known. See, e.g., Devilee et al., *Cytogenet. Cell Genet.*, 41:193–201 (1986) (chromosomes #13, 18, and 21); Waye et al., *Mol. Cell Bio.*, 7:349–356 (1987) (chromosome #7); Higgins et al., *Chromosoma*, 93:77–86 (1985) (chromosome #15); Waye et al., *Nucleic Acids Res.*, 14:6915 (1986) (chromosome #17); Yang et al., *P.N.A.S., USA*, 79:6593–6597 (1982) (chromosome X); and Donis-Keller et al., *Cell*, 51:319–337 (1987) (chromosomes 1–18, 20–22, and X) which are incorporated herein by reference.

Many of these probes preferentially hybridize to target sequences that are highly repetitive on one or more specific chromosomes. Such highly repetitive target sequences are preferred for use in the present invention so that hundreds or thousands of separate probes, each of the same type, will each hybridize with one of the many copies of the repetitive target sequence, and give a high concentration of label, which provides a strong signal, on the desired chromosome. However, probes that hybridize preferentially to repetitive sequences are not very useful for the detection of structural aberrations or mutant genes, since it is unlikely that the aberrations will involve the repetitive region. If it is desired to detect such structural aberrations, then the techniques described, e.g., in Pinkel et al., supra, can be used in the present invention.

Probes directed to specific sections of chromosomes, e.g., genes, and to chromosomes with specific abnormalities are also known, as are methods for their preparation. See, e.g., Pinkel et al., supra, and Gerhard et al., *P.N.A.S., USA*, 78:3755–3759 (1981), which are incorporated herein by reference. The signal amplification techniques used by Gerhard et al. for radioactive probes may also be applied to fluorescently labeled probes.

The probes must be labeled, e.g., by nick translation with biotin-11-dUTP, and later detected by indirect immunofluorescence using a rabbit anti-biotin IgG for a first step, and a fluorescein isothiocyanate (FITC)-conjugated second goat anti-rabbit IgG as described in Popp et al., *Exp. Cell Res.*, 189:1–12 (1990), which is incorporated herein by reference. The probes may also be labeled by other standard techniques, e.g., using CY3, CY5, or rhodamine.

Preparation of the Microscope Slides

Cells are centrifuged on cleaned slides, allowed to air dry (overnight), washed with phosphate-buffered saline (PBS: 0.15M NaCl, 10 mM Na phosphate, pH 7.2), and gradually dehydrated with ethanol.

Before hybridization, the slide mounted cells are treated with 100 μg/ml RNase A in 2×SSC buffer (0.3M NaCl, 30 mM Na citrate, pH 7.2) under a coverslip for 60 min at 37° C., treated with proteinase K (0.1 μg/ml in 20 mM Tris-HCl, 2 mM $CaCl_2$, pH 7.4), for 7.5 min at 37° C., and post-fixed with 4% paraformaldehyde (in PBS, 50 mM $MgCl_2$) for 10 min, dehydrated, and kept at room temperature until used. Other protocols, such as the one described in Gerhard et al., supra, or Pinkel et al., supra, may also be used.

In Situ Hybridization

Hybridization conditions are defined by the nucleotide composition of the probe-target complex, as well as by the level and geometry of mispairings between the probe and the target. Normal hybridization conditions for probes of 10 to 250 nucleotides in length are a temperature of about 37° to 60° C. in the presence of, e.g., 1.0M sodium chloride, 60 mM sodium phosphate, and 6 mM EDTA (pH of 7.4). Such conditions are well known and can readily be altered and manipulated for specific probes and target sequences by those skilled in the art.

For each hybridization, the labeled probe(s) are mixed in a hybridization buffer containing, e.g., 60% deionized formamide, 2×SSC (SSC=0.15M NaCl/0.015M sodium citrate, pH 7), and a carrier DNA (50 times excess of salmon sperm DNA and yeast RNA). Approximately 5 to 20 $\mu$l of the, e.g., fluorescently, labeled probe mixture is used (containing 10 or 20 ng for each probe) for each hybridization. The cells in the sample are preferably in the interphase stage during hybridization.

The probes and cell samples are denatured together under a coverslip (18×18 mm) at 80° C. for 5 min in an incubator. Hybridization is then performed in a moist chamber for 10 to 20 h at 37° C. to 60° C. depending on the desired level of stringency and probe length. To remove any unhybridized probes, the slides may be washed at room temperature two or more times for 5 min each with 60% formamide, 2×SSC, and two times for 10 min each with 2×SSC. If the probes are labelled with biotin, the slides must be treated with fluoresceinated avidin to provide the fluorescent signal. Other protocols, such as the one described in Pinkel et al., supra, may also be used. The slides are now ready for scanning.

As described in Singer et al., *Proc. Natl. Acad. Sci., USA*, 79:7334-7335 (1982), the detection of the target DNA sequences within a cell requires an adequate signal-to-noise ratio, which may be accomplished by avoiding nonspecific hybridization, adventitious sticking of nucleic acids to the cellular matrix, and nonspecific association of fluorescent labels.

Implementation

In principle, it is possible to isolate optical signals of individual cells from each other using a second parameter such as light scatter, or to isolate individual nuclei using DNA fluorescence, and then to count spots generated by the FISH technique within each cell or nuclear boundary. However, we found this to be difficult because the bright nuclear DNA fluorescent signal interfered with the very faint FISH fluorescent signal, which could not be distinguished. Also, the light scatter signal can not be reliably used to isolate FISH treated cells, because the FISH technique requires a close refractive match between the cell and its surrounding medium, which results in undetectable scatter signals.

Therefore, the preferred method of determining chromosomal abnormalities measures only one parameter per probe, the fluorescent or other optical signal emitted by each labeled hybridized complex, which allows for a simple chemical protocol, simple hardware, and rapid cell scanning rates.

Optical Signal Acquisition

After mounting the prepared slide in the apparatus and selecting a protocol to define the scan area and the sampling parameters, the user then sets a threshold fluorescence signal value T for establishing the presence of a detectable signal for any signal emitted from a label in the FISH treated cells. The operator can then initiate one or more data acquisition runs to scan an area of a test slide defined in the protocol, find all of the optical signals on the slide that meet the signal threshold T, group contiguous optical signals into regions, and generate a list of digital data representing each region found, and the X and Y position of each region with respect to Home. The user places the cell sample on the stage and initiates a run by typing a key on the computer keyboard. The flow chart of FIG. 3 illustrates the general mechanical optical signal data acquisition loop as described above.

The program causes the stage to be driven to Home and then moves the stage over the test area. As the stage moves, the beam is scanned back and forth to create the scan path shown in FIG. 4. For each X direction scan strip, the optical signal emitted by the specimen is digitized by an analog-to-digital (A/D) converter at a sample rate set by the protocol to create a sequence of digital data. Typically 450,000 such optical signals are digitized and stored in a buffer memory within 3 seconds. Data acquisition and processing may be done sequentially or simultaneously.

Digital Data Processing

The optical, e.g., fluorescent, signal obtained from cell samples treated with the FISH technique must be processed to provide useful information for the operator. This processing is preferably carried out by software which performs the steps shown in the flow chart of FIG. 5 and described in greater detail below.

Figure 5:
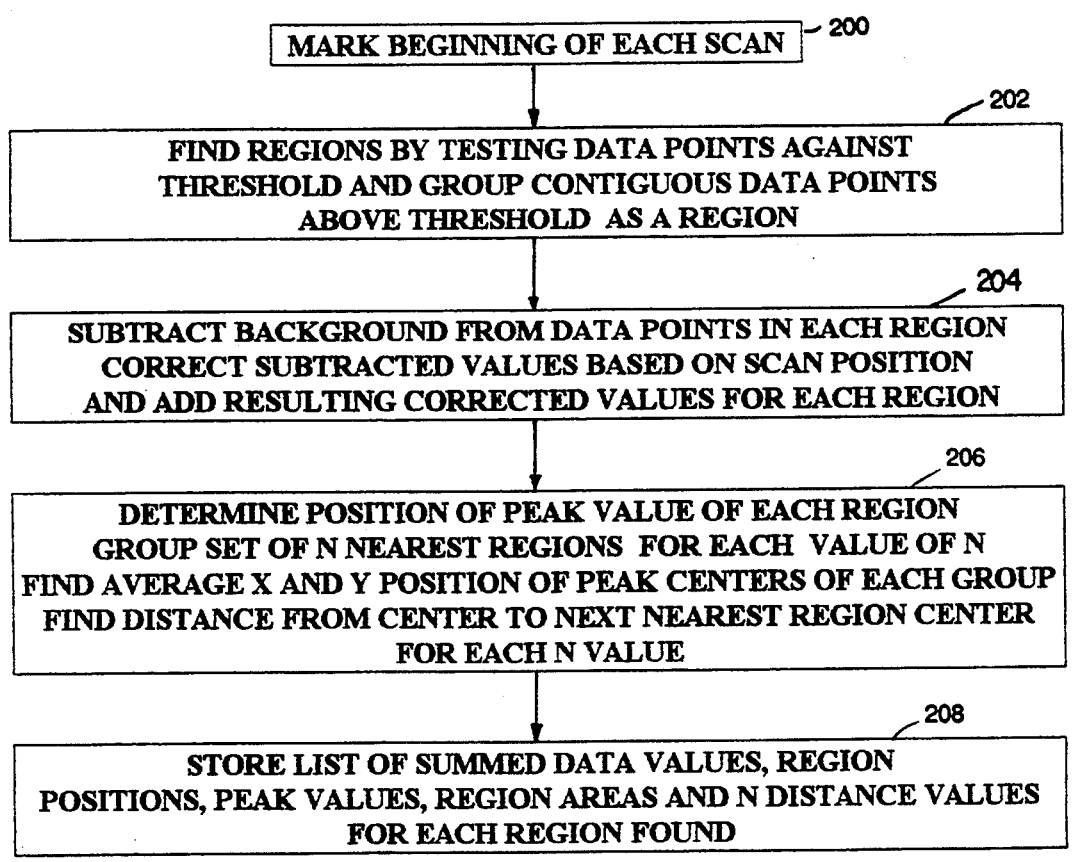
FIG. 5 is a flow chart of the data processing function steps used to manipulate digital data stored in memory.

The first data processing program function step, 200 in FIG. 5, locates the beginning of each forward scan (typically 5000 per strip) in the strip. One of the signals has added to it a synchronization pulse of sufficient amplitude, duration, and negative polarity so that it can be distinguished from all normal signals. The synchronization pulse is derived directly from the mirror scan driver 70, occurring once for each forward scan at the same time for every scan and near its beginning so that this pulse does not interfere with the actual data. In the described embodiment, only the middle (approximately 60) sample points of the 100 sample scan (i.e., there are 100 samples per scan length L) are used and will be referred to as POINTS. The program first searches successive memory locations of the buffer for values below a value to find the synchronization pulses and produces a table of pointers to all of these locations. The starting location of every data POINT value is fixed at a known displacement in the buffer from each of these pointer locations. Because the relationship of the synchronization signal and scan position is fixed, the start position of every scan can be marked and the data buffer values can each be associated with a specific scan position by appropriate record keeping in the program.

Once the digital data is stored, and scans are properly organized in the computer memory, the data is processed by a variety of protocol controlled functions to correct the data, e.g., for background, and to generate the desired distance parameters as described below. These function steps are shown in the flow chart of FIG. 5.

The second step, 202 in FIG. 5, is to find and isolate the digital data "regions" that correspond to each of the small (approx. 2 micron) fluorescent "spots" in a cell sample treated with the FISH technique, which may be very close to each other. A background value is initially determined by finding the n lowest signal values of each scan pixel of the first few scans and averaging these n values. In this second step, the program determines the pixel number, or position along the scan line, where the threshold fluorescence signal value T is exceeded by the signal less background, and again the pixel number, or position along the scan line, where the signal less background is smaller than T. This is repeated for successive scans until the signal no longer exceeds T.

Figure 6:
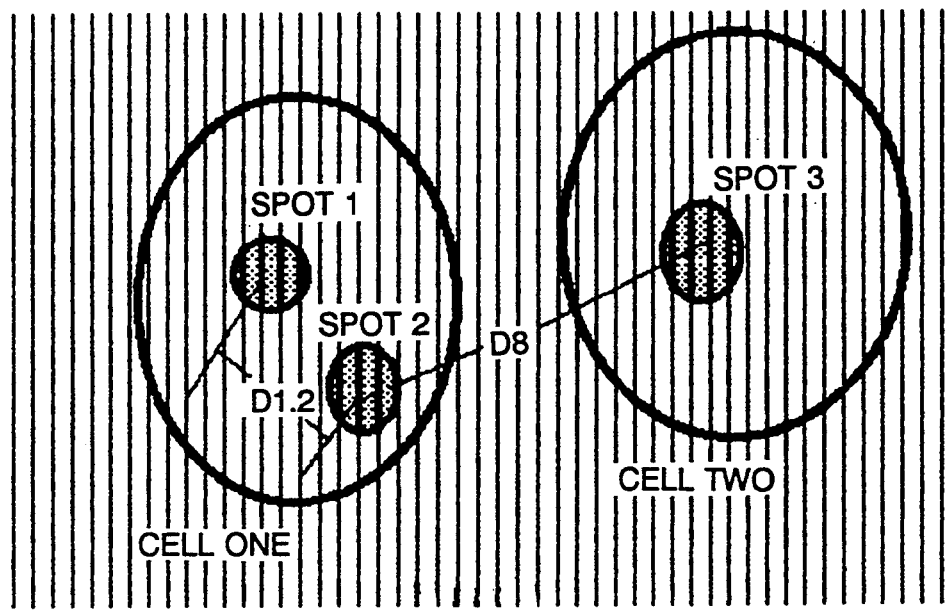
FIG. 6 is a schematic of two cells scanned by the laser scanner microscope of the invention.

Pixels of contiguous scans exceeding T are grouped together and are now processed as one "region," as described for the "neighborhoods" in the Kamentsky et al. patents, to generate properties, such as the integrated value and distance parameters, for that region. This is illustrated in FIG. 6, which schematically shows how two cells, one with two fluorescent spots and the second with one fluorescent spot, are scanned. The thin vertical lines are the scan lines. The heavy portion of the scan lines show the areas above threshold T which form the separate regions. The distance parameters are $D_{1,2}$ for spots 1 and 2 in the first cell, and $D_3$ for the single spot 3 in the second cell. Background is recomputed for each region at this time using scans adjacent to, but not including, the region.

The third step, 204 in FIG. 5, is to calculate the integrated fluorescence from each region. Corrections, e.g., for background, are performed and parameters are generated for each region as described in the Kamentsky et al. patents as if they were entire cells. For example, a center pixel is determined for each region and the digital values are corrected based on the scan position of this pixel. For each region found, the corrected, integrated intensity is determined by adding the corrected pixels in the region. This intensity value is proportional to the number of copies of the target DNA sequence that preferentially hybridizes with the DNA probe used in the FISH procedure in each region.

The fourth step, 206 in FIG. 5, is to generate an $N=x$ distance parameter, where N is the number of regions that are grouped together. This distance parameter is proportional to the distance between (1) an average, or other related position measure, of the peak value of each of one, two, three, or more spots (regions) grouped into a region group, and (2) the next nearest neighboring region to this group. For $N=1$, the distance parameter is the distance between the two closest regions in the digital data, i.e., each region is its own group. For $N=2$, the distance parameter is the distance between a point halfway between the two closest adjacent regions, i.e., $N=2$ regions together form a group, and the third closest adjacent region. For $N=x$, the distance parameter is the distance between a point at the center of the group of the first most adjacent x regions, and the $x+1$st region. The present method avoids the need to count the number of fluorescent spots per cell, as in the prior art manual counting methods.

For each region found in the scan strip, a list of property values is determined and stored in computer memory. These values include the integrated intensity, the number of pixels above threshold, the peak intensity, and the scan pixel and X and Y step position of each found region. Inter-scan pixel and X step distance values are scaled using appropriate multiplication factors so that these two distance values are equally dimensioned when combined to calculate the distance parameter. The record containing this list of values is processed one region at a time and combined with the lists of a given number of neighboring regions to form a property value list for each region group, which is used to compute the distance between that region group and its nearest neighboring region.

A new distance parameter based on the computed distance between the digital data regions is added to the list for every region. For example, if a probe that preferentially hybridizes to the X chromosome is employed, and the sample is from a normal male, the $N=1$ distance parameter will be the distance between two neighboring cells, because males have one X chromosome per cell. If the specimen were from a normal female, each cell would contain two X chromosomes, and the distance would be the distance between the two chromosomes in the nucleus, and thus smaller than the nuclear diameter of the cell. Thus the distance parameter is an indicator of the number of a given type of chromosome per cell, in this case distinguishing cells with one chromosome from those with two chromosomes, i.e., males from females.

Figure 7B:
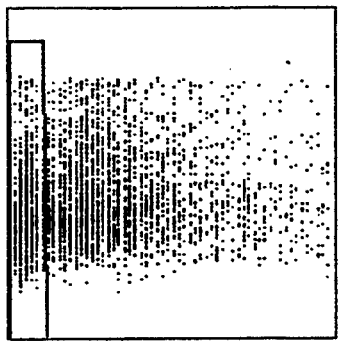
Figure 7B:
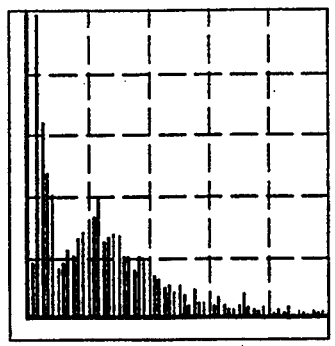
Figure 7D:
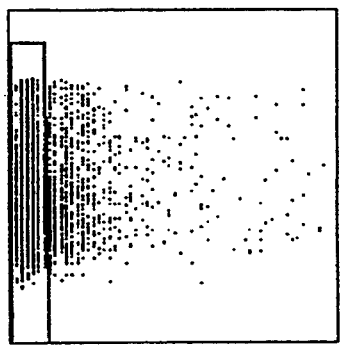
Figure 7D:
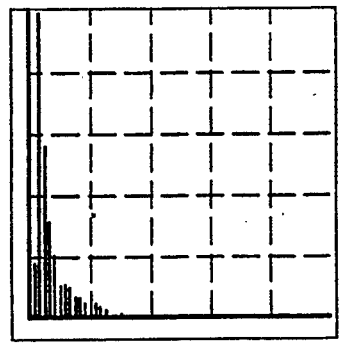

The use of the $N=1$ distance parameter is shown in the series of monitor displays in FIGS. 7A–D for samples of male and female blood cells treated with the FISH technique using a DNA probe that preferentially hybridizes to a target region of DNA on the X chromosome. The female cells have two X chromosomes, while the male cells have one. The monitor displays in FIGS. 7A and 7C show peak fluorescence versus spot distance, whereas the displays in FIGS. 7B and 7D show spot count per spot distance value. FIGS. 7A and 7B show the male sample, and FIGS. 7C and 7D show the female sample.

FIGS. 8A–F show a second set of tests, with different staining conditions, in which female cells (FIGS. 8A and 8B), male cells (FIGS. 8C and 8D), and a mixture of half male and half female cells (FIGS. 8E and 8F) were scanned, and regions along the distance parameter axis were used to perform a differential count after calibration with 100% and 0% samples. The monitor displays in FIGS. 8A, 8C and 8E show peak fluorescence versus spot distance, whereas the displays in FIGS. 8B, 8D and 8F show spot count per spot distance value. We found the distance parameter to be robust against problems in the FISH protocol such as irrelevant spots or overlapping spots, because of the large number of cells in the sample population.

The same procedure can be extended to groups of $N=x$ spots, or regions in the data, where x is greater than one, by grouping x neighboring regions into region groups, and finding for each region group its nearest adjacent $x+1$ region. The distance between the average scan and X step position of the individual regions within this region group and its nearest neighboring region is computed. Group positions can also be based on measures other than the average of the scan and X step position. In addition, measures of adjacent scan strips may be combined to produce inter-strip distances. In this manner, the N distance parameters can be added to the list along with neighboring region distances.

An alternative distance calculation method where N is greater than one, is to find the distance to the Nth closest region where N is the number of regions grouped together. The distance parameter for a region is then proportional to the distance between that region and the Nth closest region. For $N=x$, the distance parameter is calculated by finding and ignoring the $x-1$ regions closest to the region in question, and then determining and recording the distance from that region to the xth closest region.

In another example, if a probe to chromosome 21 is employed, and the sample is from a normal individual, the $N=2$ distance parameter will be the distance between that cell and its neighboring cell since normal individuals have two chromosomes 21 per cell, and the distance parameter is the distance between a point midway between the group of two closest regions, e.g., chromosomes 21, which are in one cell nucleus, and the next closest third region, which would be in an adjacent cell.

If the specimen is from a Down's Syndrome individual, each cell would contain three chromosomes 21, and the N=2 distance would be the distance between a point halfway between the two closest chromosomes 21 in the nucleus, and the third chromosome 21, also in the nucleus. The distance parameter is thus smaller than the nuclear diameter of the cells. Thus, the N=2 distance parameter is an indicator of abnormal numbers of given chromosomes, in this case distinguishing cells with two chromosomes from those with three chromosomes, i.e., normal from Down's Syndrome individuals.

The distance parameter can also be set to include further information by the use of multiple fluorescence determinations. Cells stained with two different probes, each tagged with a different dye such as CY3 and fluorescein and emitting energy at different wavelengths when excited by one or more lasers, can be scanned to define regions that can be independently located simultaneously for each cell, and the distance between them determined.

When using multiple probes in which different wavelength fluorescence emissions can be distinguished, these distance parameters can be determined and used to detect cells with translocations. If, for example, a probe that preferentially hybridizes to a particular chromosomal segment is employed and a second probe to a segment normally found on a different chromosome is also employed, and the sample is from a normal individual, the distance parameter will be the distance between the two chromosomes. If the specimen were from an individual in which a portion of a chromosomal segment containing one probe sequence is translocated to the other chromosome containing the second probe sequence, the distance parameter would be the distance along the same chromosome, and thus smaller than a given standard distance value, on the order of less than 2 microns, representing an average inter-chromosomal distance. Thus the distance parameter is an indicator of a chromosomal abnormality, a translocation.

In a final fifth step, 208 in FIG. 5, the summed data values, region positions, peak values, region areas, and N distance parameter values are stored in a list for each region found.

Display and Storage of Optical Parameters

Through the use of a display protocol, the operator can select two of the properties listed for each region, e.g., integrated intensity and the distance parameter, to be displayed on a monitor screen as a dot representing each region, with x and y positions proportional to each of the properties. Alternatively or simultaneously, the operator can request the display of a population distribution of a property such as the total number of regions for each value of a given distance parameter versus a distance parameter as shown in FIGS. 7A-D. This display is generated at the conclusion of the computation of digital values from a complete scan strip.

The property list is also stored in a protocol-named computer disk file along with a header describing the instrument protocol employed. After moving the stage in the y direction, a new strip is scanned, new region parameters are found, and they are added to the list and additional dots or counts are accumulated, until either a set number of regions is found or a set area of the slide is scanned. Typically, 500 to 5000 regions are found, processed, and stored on disk in one complete run.

During a run, or after its conclusion, the operator can, e.g., with a mouse, define polynomial areas on the monitor display, and cells within each of these areas can be counted. The instrument has the capability to nest property displays so that additional displays can be generated resulting from cells within a defined area of a previous display. This can be used to differentially count the numbers of cells with defined properties, for example, those with copy numbers above a threshold level and having distances to their neighboring region smaller than the nuclear diameter. This technique can be used to define cell data to be used to control the position of the microscope stage since the position of each region is included in the property list. The operator can also program the instrument to stop each time a cell is found with given properties, for example, to view the cell directly or by means of a CCD camera. Alternatively, the instrument can be used to reread a data file at the conclusion of a run to review the slide to show the user selected cells with defined property sets.

Other Embodiments

Another, though less preferred embodiment, may be used when accurate DNA sequence copy numbers are not required and fluorescent signal strengths are adequate. This method involves distinguishing cells with, e.g., three fluorescent spots from those with, e.g., two spots, but does not allow matching the spot size and sampling rate. In this alternative method, the slide is scanned at high resolution by a sensitive video camera (e.g., the Sony XC57) mounted on a standard fluorescence microscope. In this embodiment, the operator visually locates an area on the slide containing cell samples. Using a standard microscope arc lamp as the light source with appropriate excitation and barrier filters to view a fluorescent image of the cells, the operator changes the viewing light path from visual to video camera viewing. Excitation filters are used between the lamp and the cell sample slide to select the wavelength from the arc lamp that is best absorbed by the fluorescent dye used, e.g., 490 nm for fluorescein. Barrier filters are used in front of the camera lens to select the light emitted by the dye and to discriminate it from the excitation energy, e.g., 530 nm for fluorescein.

The video images can be digitized by a circuit board called a frame grabber, now available as a standard card for IBM compatible PCs (e.g., the Cortex-1, Imagenation Corp., Vancouver Wash.), into a pixel array in a block of computer memory representing fluorescence at each pixel in the scanned field. The operator could at this point change lamp excitation and/or barrier filters to grab a second frame of pixels representing the fluorescence from a second dye to be stored in a second block of computer memory.

If each column of pixels represented in computer memory is considered to be a scan and successive columns are considered as resulting from steps of the stage, the above "Implementation" section applies identically to this alternative method. The use of background correction is preferred, but may not be essential if the only result required is a per cell spot count. Intensity correction is similarly unnecessary for per cell spot counting.

While the invention has been described in conjunction with the detailed description thereof, this description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A method of determining the number of a specific type of chromosome per cell in a sample of cells comprising (a) fixing the cell sample on a substrate,
(b) contacting the cell sample with a nucleic acid probe comprising a detectable label under conditions that allow said probe to hybridize preferentially to a target nucleotide sequence within said specific type of chromosome in said cells to form a hybridized complex, wherein each complex forms a labeled region,
(c) detecting each labeled region in the sample,
(d) assigning a position corresponding to each labeled region on the substrate,
(e) defining a predetermined number of nearest adjacent labeled regions as a region group and assigning a position on the substrate to each region group derived from said labeled region positions,
(f) generating a distance parameter for each region group based on the distance between the position of a region group and the position of the next nearest adjacent labeled region and recording the distance parameter for each region group in the sample, and
(g) comparing a population distribution of the distance parameters to a value based on the cellular nuclear diameter, and determining whether the closest regions are within the same cell, to determine the number of a specific type of chromosome per cell in the cells of the sample.

2. A method of determining the number of a specific type of chromosome per cell in a sample of cells comprising
(a) fixing the cell sample on a substrate,
(b) contacting the cell sample with a nucleic acid probe comprising a detectable label under conditions that allow said probe to hybridize preferentially to a target nucleotide sequence within said specific type of chromosome in said cells to form a hybridized complex, wherein each complex forms a labeled region,
(c) detecting each labeled region in the sample,
(d) assigning a position corresponding to each labeled region on the substrate,
(e) defining a predetermined number N of labeled regions as a region group,
(f) generating a distance parameter for a selected labeled region based on the distance between the position of said selected labeled region and the position of the Nth closest labeled region, wherein the Nth closest labeled region is the Nth labelled region numbered sequentially by increasing distance from said selected labeled region, and recording the distance parameter for each labeled region in the sample, and
(g) comparing a population distribution of the distance parameters to a value based on the cellular nuclear diameter, and determining whether the closest labeled regions are within the same cell, to determine the number of a specific type of chromosome per cell in the cells of the sample.

3. The method of claim 1 or 2, wherein said target nucleotide sequence is unique to a specific chromosome, said predetermined number of labeled regions in a region group is two, and said comparison step provides a determination of the number specific chromosomes in the cells of the sample, and wherein a distance parameter greater than said cellular nuclear diameter value indicates two chromosomes per cell, and a distance parameter less than said cellular nuclear diameter value indicates more than two chromosomes per cell, and indicates a genetic abnormality.

4. The method of claim 3, wherein said target sequence is unique to chromosome 21, and wherein cells having more than two chromosomes per cell indicate Down's Syndrome.

5. The method of claim 1 or 2, wherein said target nucleotide sequence is unique to a specific type of chromosome, said predetermined number of labeled regions in a region group is one, and said comparison step provides a determination of the number of specific chromosomes in the cells of the sample, and wherein a distance parameter greater than said cellular nuclear diameter value indicates one chromosome per cell, and a distance parameter less than said cellular nuclear diameter value indicates more than one chromosome per cell.

6. The method of claim 5, wherein said target sequence is unique to chromosome X, and wherein cells having only one X chromosome per cell are from a male.

7. The method of claim 1 or 2, wherein more than one type of probe is used, each type of probe hybridizing preferentially to a unique target nucleotide sequence in said cells, and each type of probe having a unique detectable label, and wherein each of method steps (b) to (e) and (g) are carried out for each type of probe, and in method step (f) said labeled region corresponds to a first type of probe and said next neighboring labeled region of claim 1 and said Nth closest labeled region of claim 2 corresponds to a second type of probe.

8. The method of claim 1 or 2, wherein said cell sample is obtained from a mammal.

9. The method of claim 1 or 2, wherein said cell sample is obtained from a fetus.

10. The method of claim 1 or 2, wherein said label is fluorescent.

11. The method of claim 10, wherein said fluorescent label is fluorescein, rhodamine, or a cyanine dye.

12. The method of claim 1 or 2, further comprising the step of defining a threshold level below which no label is detected, and said label detecting step comprises measuring a level for each label in the sample, if any, and comparing the label level with said threshold level, a label being detected only when its level is above said threshold level.

13. A method of determining the number of a specific type of chromosome per cell in a sample of cells comprising
(a) fixing the cell sample on a substrate,
(b) contacting the cell sample with a nucleic acid probe comprising a detectable label under conditions that allow said probe to hybridize preferentially to a target nucleotide sequence within said specific type of chromosome in said cells to form a labeled hybridized complex,
(c) scanning the cell sample with a laser beam to generate an optical signal,
(d) detecting the optical signal and digitizing the detected signal to produce a set of digital data points,
(e) storing said set of digital data points,
(f) locating a region within the stored set of digital data points, said region comprising contiguous data points with digital values above a predetermined threshold value representing a labeled complex,
(g) assigning a position corresponding to each region on the substrate, (h) defining a predetermined number of nearest adjacent regions as a region group and assigning a position on the substrate to each region group derived from said region positions,
(i) generating a distance parameter for each region group based on the distance between the position of a region group and the position of the next nearest adjacent region,
(j) recording the distance parameter for each detected region group, and
(k) comparing a population distribution of the distance parameters to a value based on the cellular nuclear diameter, and determining whether the closest regions are within the same cell, to determine the number of a specific type of chromosome per cell in the cells of the sample.

14. A method of determining the number of a specific type of chromosome per cell in a sample of cells comprising
(a) fixing the cell sample on a substrate,
(b) contacting the cell sample with a nucleic acid probe comprising a detectable label under conditions that allow said probe to hybridize preferentially to a target nucleotide sequence within said specific type of chromosome in said cells to form a labeled hybridized complex,
(c) scanning the cell sample with a laser beam to generate an optical signal,
(d) detecting the optical signal and digitizing the detected signal to produce a set of digital data points,
(e) storing said set of digital data points,
(f) locating a region within the stored set of digital data points, said region comprising contiguous data points with digital values above a predetermined threshold value representing a labeled complex,
(g) assigning a position corresponding to each region on the substrate,
(h) defining a predetermined number N of regions as a region group,
(i) generating a distance parameter for a selected region based on the distance between the position of said selected region and the position of the Nth closest region, wherein the Nth closest region is the Nth region numbered sequentially by increasing distance from said selected region,
(j) recording the distance parameter for each detected region, and
(k) comparing a population distribution of the distance parameters to a value based on the cellular nuclear diameter, and determining whether the closest detected regions are within the same cell, to determine the number of a specific type of chromosome per cell in the cells of the sample.

15. The method of claim 13 or 14, wherein said target nucleotide sequence is unique to a specific type of chromosome, said predetermined number of regions in a region group is two, and said comparison step provides a determination of the number of specific chromosomes in the cells of the sample, and wherein a distance parameter greater than said cellular nuclear diameter value indicates two chromosomes per cell, and a distance parameter less than said cellular nuclear diameter value indicates more than two of said specific chromosomes per cell, and indicates a genetic abnormality.

16. The method of claim 13 or 14, wherein said target nucleotide sequence is unique to a specific type of chromosome, said standard distance value is based on the cellular nuclear diameter, said predetermined number of regions in a region group is one, and said comparison step provides a determination of the number of specific chromosomes in the cells of the sample, and wherein a distance parameter greater than said cellular nuclear diameter value indicates one chromosome per cell, and a distance parameter less than said cellular nuclear diameter value indicates more than one chromosome per cell.

17. The method of claim 13 or 14, further comprising steps of
(a) summing the digital values in each region for each probe, and
(b) recording the summed digital values for each probe, wherein said values are proportional to the DNA copy number.

18. The method of claim 13 or 14, further comprising the step of moving the microscope stage to the assigned position of a region having a specific distance parameter so that the operator may observe cells visually.

19. The method of claim 13 or 14, wherein said optical signal is fluorescence.

20. The method of claim 13, wherein the position assigned to a region group corresponds to an average of the positions of peak intensity value of each region in said region group.

21. A method of determining whether two or more different specific nucleic acid probes in a cell in a sample of cells are on the same chromosome, comprising
(a) fixing the cell sample on a substrate,
(b) contacting the cell sample with a first nucleic acid probe comprising a detectable first label under conditions that allow said probe to hybridize preferentially to a first target nucleotide sequence within a chromosome in said cells to form a first labeled hybridized complex,
(c) contacting the cell sample with a second nucleic acid probe comprising a detectable second label under conditions that allow said probe to hybridize preferentially to a second target nucleotide sequence within a chromosome in said cells to form a second labeled hybridized complex,
(d) scanning the cell sample with a first laser beam having a first wavelength to excite said first label and generate a first optical signal,
(e) scanning the cell sample with a second laser beam having a second wavelength to excite said second label and generate a second optical signal,
(f) detecting and digitizing said first and second optical signals to produce two sets of digital data points,
(g) storing said sets of digital data points,
(h) for each data set, locating a region within the stored set of digital data points, said region comprising contiguous data points with digital values above a predetermined threshold value representing a labeled complex,
(i) for each data set, assigning a digital position corresponding to each region on the substrate,
(j) generating a digital distance parameter for a region based on the distance between the position of said region in said first data set to the nearest region in the second data set,
(k) recording the distance parameter for each detected region in the first data set, and
(l) comparing a population distribution of the distance parameters of the first data set to a value equal to an average inter-chromosomal distance in said cells to determine whether said first and second probes are on the same chromosome.

22. The method of claim 21, wherein said first wavelength and second wavelength laser beams scan the cell sample at a different time.

* * * * *

UNITED STATES PATENT AND TRADEMARK OFFICE
CERTIFICATE OF CORRECTION

PATENT NO. : 5,427,910

DATED : June 27, 1995

INVENTOR(S) : Louis A. Kamentsky et al.

It is certified that error appears in the above-identified patent and that said Letters Patent is hereby corrected as shown below:

Cover page, [56] References Cite, OTHER PUBLICATIONS, the "Cell Biology" reference, "Alhyn" should be --Allyn--.

Col. 6, line 14, "FIGS. 8A-E" should be --FIGS. 8A-F--.

Col. 6, line 14, after "are", delete "is".

Col. 17, line 61, after "specific", inset --type of--.

Col. 18, line 1, after "two" insert --of said specific--.

Col. 20, line 60, "(1)" should be --(1)--.

Signed and Sealed this

Nineteenth Day of August, 1997

Attest:

BRUCE LEHMAN

Attesting Officer

Commissioner of Patents and Trademarks